United States Patent [19]

Pivawer

[11] 4,163,753
[45] Aug. 7, 1979

[54] PROCESS FOR THE SIMULTANEOUS PREPARATION OF AROMATIC ACID CHLORIDES AND ALIPHATIC ACID CHLORIDES

[75] Inventor: Philip M. Pivawer, Hamden, Conn.

[73] Assignee: Diaz Chemical Corporation, Holley, N.Y.

[21] Appl. No.: 768,330

[22] Filed: Feb. 14, 1977

[51] Int. Cl.$^2$ .................. C07C 51/00; C07C 53/14; C07C 63/10
[52] U.S. Cl. .................. 260/544 D; 260/544 L
[58] Field of Search .................. 260/544 D, 544 L

[56] References Cited

U.S. PATENT DOCUMENTS

| | | | |
|---|---|---|---|
| 1,793,917 | 2/1931 | Faber | 260/610 D |
| 1,965,556 | 7/1934 | Mills | 260/544 Y |
| 2,016,784 | 10/1935 | Kraenzlein | 260/543 R |
| 3,282,989 | 11/1966 | Renckhoff et al. | 260/544 D |
| 3,284,488 | 11/1966 | Renckhoff et al. | 260/544 D |
| 3,835,187 | 9/1974 | Dyson | 260/544 D |

OTHER PUBLICATIONS

Chemical Abstract, vol. 82, col. 139, 750(f).
Merck Index, pp. 6-7, 7th Ed., (1967).
Morrison & Boyd, "Organic Chemistry," pp. 668-669, (3rd. Ed.), (1974).

*Primary Examiner*—Gerald A. Schwartz
*Attorney, Agent, or Firm*—Mattern, Ware, Davis & Stoltz

[57] ABSTRACT

By reacting an aromatic compound containing at least one trichloromethyl group bonded to an aromatic carbon atom with an aliphatic acid anhydride in the presence of a catalyst, an aromatic acid chloride and an alkyl carboxylic acid chloride are produced. The desirable products are preferably obtained through distillation at ambient conditions. Although various catalysts can be employed, an acid catalyst, such as sulphuric acid is preferred.

19 Claims, No Drawings

PROCESS FOR THE SIMULTANEOUS PREPARATION OF AROMATIC ACID CHLORIDES AND ALIPHATIC ACID CHLORIDES

BACKGROUND

This invention relates to the simultaneous preparation of an aromatic acid chloride and an aliphatic carboxylic acid chloride.

The compounds prepared by the method of this invention are well known chemical intermediates used in the preparation of dyes, pharmaceuticals, lubricants, and polymers. Since their use has become widespread, several various methods have been developed to produce these compounds.

Generally, the aromatic acid chlorides have been more widely used and most of the prior art development has been directed to the production of aromatic acid chlorides. In spite of this attention, the methods that have been developed all suffer from various disadvantages which have plagued the production of aromatic acid chlorides until the present invention was made.

The prior art methods for preparing aromatic acid chlorides are typified by the following:

1. The reaction of an aromatic acid with thionyl chloride or phosphorus pentachloride
2. The reaction of benzaldehyde with chlorine, Chem Abstr 82,1975 155697 Netherlands patent application Ser. No. 73 06,212.
3. The reaction of α,αα-benzotrichlorides with water or benzoic acids in the presence of an acid catalyst. Japan Kokai No. 74, 132,028, Chem Abstr 82,1975 139750; U.S. Pat. Nos. 1,793,917; 2,016,784; 3,835,187.
4. The reaction of α,α,α-trichlorotoluenes with sulfur dioxide, U.S. Pat. Nos. 3,775,476 and 3,806,545; Chem Abstr. 80 26973w.

The first three methods described above, all suffer from the common disadvantage of producing stoichiometric amounts of hydrogen chloride as an unwanted byproduct which must be neutralized or destroyed in some other way. The fourth method requires the use of high pressure to effect reaction.

Therefore, it is a principle object of this invention to provide a process for producing an aromatic acid chloride without producing any undesirable products.

Another object of the present invention is to provide a process embodying the features characterized above which is capable of being conducted at ambient conditions, thereby eliminating the need for elevated pressure.

Another object of the present invention is to provide a process embodying the feature characterized above wherein an additional commercially desirable product is also produced.

A further object of the present invention is to provide a process embodying the features characterized above wherein the products are easily separated in a substantially pure form directly during the process, thereby eliminating any costly purification.

Another object of the present invention is to provide a process which is easily and inexpensively performed.

Other objects of the invention will in part be obvious and will in part appear hereinafter.

SUMMARY OF THE INVENTION

The process for the simultaneous preparation of an aromatic and aliphatic acid chloride includes the steps of:

1. Contacting an aromatic compound containing one or more trichloromethyl groups bonded to nonadjacent aromatic carbon atoms (at least one hydrogen atom must be adjacent to the carbon atom bonded to the trichloromethyl group with the other substituents taken from hydrogen, halogen, alkyl, haloalkyl, alkoxy, nitro or carbonyl chloride) with an aliphatic carboxylic acid anhydride, having from two to six carbon atoms in a straight or branched chain, in the presence of a catalyst;
2. distilling the corresponding aliphatic acid chloride; and finally,
3. recovering the resultant aromatic acid chloride.

The invention accordingly comprises the several steps and the relation of one or more of such steps with respect to each of the others thereof, which will be exemplified in the process hereinafter disclosed, and the scope of the invention will be indicated in the claims.

DETAILED DESCRIPTION

The key feature of this invention is the discovery that an aromatic compound containing one or more trichloromethyl group will react with an aliphatic carboxylic acid anhydride in the presence of a catalyst to give both an aromatic and aliphatic acid chloride. Furthermore, the aliphatic acid chloride, because of its low boiling point, can be easily distilled away from the aromatic acid chloride which in turn can easily be separated from the catalyst residue. Another advantage of this sytem is that only a stoichiometric amount of aliphatic anhydride is required, thereby eliminating the need for any recycle of this material. Still another advantage is that no costly solvents are required for the reaction or for purification.

The Aromatic Trichloromethyl Component

The trichloromethyl ($CCl_3$) compounds that can be converted into acid chlorides in the invention process may vary widely so long as the corresponding aromatic carbonyl chlorides are capable of existence and are sufficiently stable under the defined thermal conditions to be recovered from the reaction mass. They may be broadly represented as $(R)_m Ar(CCl_3)_n$, where Ar stands for an aromatic nucleus, R is H or a substituent that does not interfere with the reaction or the products, m and n are integers of at least one each which together satisfy the valence of the aromatic nucleus, and the $CCl_3$ groups are on nonadjacent carbon atoms when n is greater than one.

Thus the aromatic compounds may contain one or more trichloromethyl groups, normally one to three such groups per aromatic ring, and optionally may contain one or more other substituents inert to the acid chloride group under reaction conditions. The nuclear positions adjacent to trichloromethyl will have at least one hydrogen as a substituent. Included are compounds of the benzene, naphthalene, phenanthrene and anthracene series, also binuclear analogs thereof wherein two aryls, normally phenyls, with one or both carrying one or more trichloromethyl groups, are joined through an electron pair bond, an alkylene group such as methylene, ethylidene, propylidene or butylidene, a carbonyl group, or the like bridging group which is inert under the conditions of the reaction.

Non-interfering R substituents other than hydrogen that may be present along with the trichloromethyls in the compounds to be treated include: the halogens F, Cl, Br and I; alkyl, normally lower alkyl for reasons of availability, such as methyl, ethyl, isopropyl, tert-butyl; chloroalkyl other than trichloromethyl and normally lower chloroalkyl, such as chloromethyl, dichloromethyl and β,β,β-trichloroethyl; fluoroalkyl, such as fluoromethyl, difluoromethyl, trifluoromethyl, pentafluoroethyl, and perfluorobutyl; lower alkoxy such as methoxy, ethoxy, n-propoxyl, and n-butoxyl; and others such as carbonyl chloride, cyano and nitro.

It is possible to stepwise convert poly (trichloromethyl) compounds to the poly-acid chlorides. For example with two trichloromethyls present, as in 1,3-bis(trichloromethylbenzene), reaction temperatures can be adjusted to stepwise yield the trichloromethyl-substituted benzoyl chloride. Such product can be recovered and the still unreacted trichloromethyl groups converted in a second separate reaction or, if desired, in the same reactor by operating for longer times and/or at higher reaction temperatures. Similarly with three trichloromethyl groups present, as in 1,3,5-tris(trichloromethyl)benzene, the reaction can be controlled to yield one or more of bis(trichloromethyl)benzoyl chloride, trichloromethylisophthaloyl chloride and trimesoyl chloride.

Representative trichloromethyl compounds are:
benzotrichloride(trichloromethylbenzene),
o, m and p-chlorobenzotrichloride,
o, m & p fluorobenzotrichloride,
o, m and p-bromobenzotrichloride,
p-iodobenzotrichloride,
3,4-dichlorobenzotrichloride,
2,4-dichlorobenzotrichloride,
2,5-dichlorobenzotrichloride,
3,5-dichlorobenzotrichloride,
2,4-dibromobenzotrichloride,
2,5-dibromobenzotrichloride,
3,4-dibromobenzotrichloride,
3,5-dibromobenzotrichloride,
2,4-difluorobenzotrichloride,
3,4-difluorobenzotrichloride,
3,5-difluorobenzotrichloride,
2,5-difluorobenzotrichloride,
2,3,4; 2,3,5 or 3,4,5 trichloro, tribromo, trifluro, benzotrichloride,
2-chloro-4-fluorobenzotrichloride,
2-chloro-4-bromobenzotrichloride,
4-chloro-2-bromobenzotrichloride,
4-chloro-2-fluorobenzotrichloride,
2-chloro-3-fluorobenzotrichloride,
2-chloro-3-bromobenzotrichloride,
m-methyl-benzotrichloride (α,α,α-trichloromethyl-m-xylene),
3,4-dimethylbenzotrichloride,
p-tert-butylbenzotrichloride,
p-trifluoromethylbenzotrichloride,
m-dichloromethylbenzotrichloride (α,α,α,α',α'-pentachloro-m-xylene),
p-methoxybenzotrichloride,
m-ethoxybenzotrichloride,
p-n-butoxybenzotrichloride,
m-cyanobenzotrichloride,
m-nitrobenzotrichloride,
m-trichloromethylbenzoyl chloride (α,α,α-trichloro-m-toluyl chloride),
p-trichloromethylbenzoyl chloride,
1,3-bis(trichloromethyl)benzene (α,α,α,α',α',α'-hexachloro-m-xylene),
5-chloro-1,3-bis(trichloromethyl)benzene,
1,4-bis(trichloromethyl) benzene,
4-chloro-1,3-bis(trichloromethyl)benzene,
2,5-dichloro-1,4-bis(trichloromethyl)benzene,
2-chloro-1,3-bis(trichloromethyl)benzene,
2-chloro-1,4-bis(trichloromethyl)benzene,
4,5-dichloro-1,3-bis(trichloromethyl)benzene,
4,6-dichloro-1,3-bis(trichloromethyl)benzene,
2,5-dichloro-1,3-bis(trichloromethyl)benzene,
4,5,6-trichloro-1,3-bis(trichloromethyl)benzene,
1,3,5-tris(trichloromethyl)benzene (α,α,α,α',α',α',α'',α''-nonachloromesitylene),
1-trichloromethylnaphthalene,
1,5-bis(trichloromethyl)naphthalene,
2-trichloromethylphenanthrene,
1-trichloromethylanthracene,
p-trichloromethylbiphenyl,
p,p'-bis(trichloromethyl)biphenyl,
bis(p-trichloromethylphenyl)methane,
2,2-bis(p-trichloromethylphenyl)propane, and
p,p'-bis(trichloromethyl)benzophenone.

Trichloromethyl compounds of the benzene series, which may contain halo, alkyl, chloroalkyl, fluoroalkyl, alkoxyl and carbonyl chloride groups, represent an important reactant class, expecially 1,3-bis(trichloromethyl)benzene and 1,4-bis(trichloromethyl)benzene, since the corresponding acid chlorides enjoy wide utility. It will be noted that the hexachloro meta- and p-xylenes obtained by side chain chlorinating the parent aromatic hydrocarbons may contain ring chlorinated derivatives, as exemplified above. Such ring chlorinated trichloromethyl-containing materials may also be converted simultaneously to the corresponding ring chlorinated acid chlorides by the process of this invention.

The Aliphatic Carboxylic Acid Anhydride

Generally, the aliphatic carboxylic acid anhydride takes the following form: R—C=O—O—C=O—R, where R is a straight or branched carbon atom chain with between about one and six carbon atoms. However, acetic anhydride ($CH_3C$=O—O—$CH_3$) is preferred and is believed to be the most practical, since acetyl chloride will be produced and have a large demand.

Of course, other aliphatic carboxylic acid anhydrides can be successfully used in the process of the present invention. Such aliphatic carboxylic acid anhydrides include propionic anhydride, butyric anhydride, isobutyric anhydride, valeric anhydride, isovaleric anhydride, and pivalic anhydride. A cyclic carboxylic anhydride such as glutaric anhydride may also be used. As is more fully defined below, in each case 2 moles of the corresponding acid chloride is produced for each trichloromethyl group which is present, except in case of glutaric anhydride where only one mole of acid chloride is produced.

The Catalyst

It is envisioned that concentrated sulfuric acid will be the catalyst of choice with the concentration ranging from 0.0005 to 10 mole % based on the trichloromethyl concentration. The preferred catalyst range is from 0.01 to 5% with the most preferred range from 0.1 to 1.5%. Preferably, only acid catalysts are employed, and other than sulfuric, phosporic acid has been found to work equally as well.

PROCESS

In the basic procedure of the present invention, the two reactants, namely the aromatic trichloride compound and the alkyl carboxylic anhydride are mixed together with a catalyst and heated. The actually reactant mixing can be achieved either initially or over a period of time with one reactant being added to the other.

Although various recovery methods for obtaining the two products are well within the knowledge of one skilled in the art, it has been found that distillation provides the most direct and inexpensive recovery procedure. Consequently, the mixed reactants are heated until the aliphatic acid chloride produced begins to vaporize. The aliphatic acid chloride is then recovered through distillation which continues until all of the aliphatic caboxylic acid anhydride has been converted to the corresponding aliphatic acid chloride.

The purity of the aliphatic acid chloride produced can be optimized by either maintaining the temperature of the vapor pressure substantially equal to the boiling point of the aliphatic acid chloride until all of the aliphatic acid chloride has been recovered. Alternatively, if the temperature of the vapor pressure rises to a level which may allow the aromatic acid chloride to also be distilled, a reflux of the product can be employed until the proper vapor pressure temperature has been obtained. Both of these systems, as well as other methods, are well known to those skilled in the art and are clearly within the scope and purview of the process of this invention.

The process is then continued by recovering the aromatic acid chloride product of this present invention. In the preferred embodiment, the aromatic acid chloride is recovered by distillation. In the distillation recovery, the pot temperature is raised until the aromatic acid chloride begins to distill. The distillation procedure continues until all of the aromatic acid chloride has been recovered.

Although distillation has been found to be the most economical recovery method to employ in obtaining most aromatic acid chlorides, it is possible to obtain solid aromatic acid chloride using the process of this invention. If solid aromatic acid chlorides are to be obtained, recrystallization may be used for purification. This type of procedure is well known to those skilled in the art as well as other recovery and purification methods, the use of which is clearly within the scope of the present invention.

The following chemical equation outlines the basic reaction of the present invention:

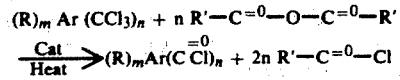

As can be seen from this chemical equation, the maximum yields are obtained when the aliphatic carboxylic acid anhydride has a molar amount equal to the number of trichloromethyl groups which are bonded to the aromatic compound.

Experiments have shown that although a one-to-one ratio is preferred, amounts ranging between 0.8 to 1.2 moles of the trichloromethyl group are completely compatible with 1 mole of the aliphatic carboxylic acid anhydride. However, the reaction will proceed with even higher or lower ratios, with merely varing ratios of the desired products being obtained.

If an excess of anhydride is used, the excess anhydride will be recovered during the distillation and must be separated from the aliphatic acid chloride and the aromatic acid chloride. On the other hand, if an excess of the aromatic compound having one or more trichloromethyl groups bonded to non-adjacent carbon atoms of the aromatic ring is used in the reaction, the higher boiling unreacted aromatic compound will be left in the reactor, provided careful fractionation of the generally lower boiling aromatic acid chloride is employed. This unreacted compound is then utilized in a subsequent run without clean-out of the reactor.

Generally, it has been found that fresh catalyst should be added before the start of each run. Also, an inert atmosphere such as dry air or nitrogen is beneficial for high yield, but is not an essential requirement for the process.

The following examples are included to show various experimental runs which have been conducted employing the process of the present invention. These examples are included for illustrative purposes only and are not in any way intended to be considered or interpreted as a limitation of the present invention. Various other compounds and conditions, some of which are described above, may be employed with similarly advantageous results by using the teaching of the present invention. Consequently, the scope of the present invention is intended to cover all of the variations.

The following chemical equation outlines the particular reaction which is occurring in examples 1-4.

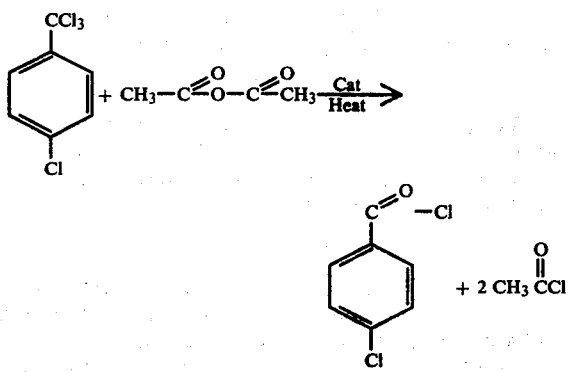

Of course, this reaction, as well as the reactions occurring in the other examples, are all specific reactions included within the overall generic reaction described above.

The following examples demonstrate the various embodiments of the invention.

EXAMPLE 1

Charge to stirred reactor 229 g (1.0 mole) p-chlorobenzotrichloride, 93 g (0.9 mole) acetic anhydride and 1.0 g conc sulfuric acid. The reaction mixture was maintained in a nitrogen atmosphere and gradually heated to 128° C. when acetyl chloride began distilling. Acetyl chloride (135.5 g, 94.7%) was collected over a temperature range of 50°-64° C. The reaction mixtue was heated further and the p-chlorobenzoyl chloride was distilled over a temperature range from 226 to 230° C. with the pot temperature rising from 237° to 255° C. The yield of product was 141 g (81%).

EXAMPLE 2

To the reaction from example 1 without cleanout was added p-chlorobenzotrichloride (231 g, 1.0 mole), acetic anhydride (83.5 g, 0.82 mole) and sulfuric acid (1.0 g, 0.01 mole). The reaction was run similar to example 1. An additional 1.0 g of sulfuric acid was added after all of the acetyl chloride had been removed. The yield of acetyl chloride was 120 g (93.4%) and the yield of p-chlorobenzoyl chloride was 176.3 g (100%).

EXAMPLE 3

To the reactor residue from run 2 was added 230 g (1.0 mole) of p-chlorobenzotrichloride and 96.5 g (0.945 mole) of acetic anhydride. Sulfuric acid was placed in an addition funnel but not added to the reaction. The mixture was heated to 135° C. but no reaction occurred. The mixture was cooled to 90° C. and the sulfuric acid was added. The reaction mixture was again heated to 130° C. and acetyl chloride began to distill. A 91.3% yield was obtained with the reaction temperature heated to 200° C.

At this point the reaction was stopped and cooled back to room temperature. Two days later the mixture was again heated to give 157 g (90%) of p-chlorobenzoyl chloride.

EXAMPLE 4

To the reaction residue from run 3 was added 230 g of p-chlorobenzotrichloride, 97 g of acetic anhydride and 2 g of sulfuric acid (98%). The reaction was carried as previously described to give 136 g (91.2%) of acetyl chloride and 177 g (101%) of p-chlorobenzoyl chloride. The average yield from runs 1–4 was 92.7% for acetyl chloride and 93% for p-chlorobenzoyl chloride.

EXAMPLE 5

The procedure in run 1 was repeated using propionic anhydride (119 g, 0.92 mole) in place of acetic anhydride. A 97% yield of propionyl chloride and a 61% yield of p-chlorobenzoyl chloride were obtained.

EXAMPLE 6

Benzotrichloride (195.5 g), acetic anhydride (98 g) and sulfuric acid were charged to the reactor. Acetyl chloride began to distill when the reaction mixture reached 118° C. The yield of acetyl chloride was 130 g (86.3%) and the yield of benzoyl chloride was 130.9 g (93.1%), b.p. 191°–193° C.

EXAMPLE 7

The reaction as described in run 1 was carried out starting with 230 g of o-chlorobenzotrichloride, 96 g of acetic anhydride, and 2 g of conc sulfuric acid to give an 87.9% yield of acetyl chloride and a 74% yield of o-chlorobenzoyl chloride b.p. 234°–238° C.

EXAMPLE 8

Benzotrichloride (195.5 g) and sulfuric acid (1.59) were charged to the reactor. Acetic anhydride (102 g) was added over a 1 hour period with the temperature between 140° and 155° C. Acetyl chloride began to distill about 5 minutes into the acetic anhydride addition and continued throughout the addition. After most of the acetyl chloride had distilled, the pot temperature was raised gradually to 200° C. over a ½ hour period and the remaining acetyl chloride was collected. Total yield 141 g (89.8%). The benzoyl chloride was then distilled, giving 89.5 g (55% yield).

EXAMPLE 9

In this run, the addition procedure was reversed with the benzotrichloride being added to the acetic anhydride and sulfuric acid over a 3 hour period. The yield of acetyl chloride was 145.59 (92.8%) and the yield of benzoyl chloride was 102 gms (72.6%).

EXAMPLE 10

The procedure was identical to that of Example 8 except that 85% phosphoric acid was used in place of sulfuric acid. The following amounts were charged to the reactor: benzotrichloride (195.5 g), acetic anhydride (102 g), phosphoric acid (2 g). The acetyl chloride was collected over a 5 hour period with the temperature rising from 122° to 210° during the distillation. The yield of acetyl chloride was 145.6 g (92.9%). Distillation of the benzoyl chloride gave 124.0 g (88.2%).

EXAMPLE 11

Bis 1,4(trichloromethyl)benzene (88 L g, 0.281 mole), acetic anhydride (65 g., 0.315 mole) and sulfuric acid (1.0 g) were mixed together and heated in a nitrogen atmosphere. Acetyl chloride (45 g, 51.7%) was collected with the pot heated from 112° to 220° C. The pot was then cooled to 110° C. and placed under 20 mm of vacuum. Terephthoyl chloride 17 g (30%) was distilled, b.p. 147°–156° C. at 16 mm.

It will thus be seen that the objects set forth above, among those made apparent from the preceding description, are efficiently attained and, since certain changes may be made in carrying out the process without departing from the scope of the invention, it is intended that all matter contained in the above description and the above examples shall be interpreted as illustrative and not in a limiting sense.

I claim:

1. A process for preparing an aromatic acid chloride and an aliphatic acid chloride comprising the following steps:

A. mixing an aliphatic carboxylic acid anhydride having the structure

where R is an aliphatic carbon chain having between one and six carbon atoms, with an aromatic compound having one or more trichloromethyl groups bonded to non-adjacent carbon atoms of the aromatic ring;

B. heating the mixture in the presence of a strong acid catalyst selected from the group consisting sulfuric and phosphoric acid, until the aliphatic carboxylic acid chloride begins to distill;

C. distilling the aliphatic carboxylic acid chloride; and

D. recovering the aromatic acid chloride from the reaction mixture.

2. The process defined in claim 1, comprising the additional steps of

E. heating the reaction mixture further, after the aliphatic carboxylic acid chloride has been recovered; and F. recovering the aromatic acid chloride by distillation.

3. The process defined in claim 1, wherein the reactants are initially completely mixed together.

4. The process defined in claim 1, wherein the entire process is conducted at atmospheric pressure.

5. The process defined in claim 1, wherein the process is conducted in an inert atmosphere.

6. The process defined in claim 5, wherein the inert atmosphere is nitrogen.

7. The process defined in claim 1, wherein one mole of aliphatic carboxylic acid anhydride is employed for each trichloromethyl group which is bonded to the non-adjacent carbon atoms of the aromatic compound.

8. The process defined in claim 7, wherein an excess of the required amount of the aromatic compound having one or more trichloromethyl groups bonded to non-adjacent carbon atoms is employed, thereby providing unreactive aromatic material which can be employed in subsequent runs without necessitating a reactor cleanout.

9. The process defined in claim 1, wherein the aroatic compound comprises benzene.

10. The process defined in claim 9, wherein the benzene compound having one or more trichloromethyl groups bonded to non-adjacent carbon atoms comprises one selected from the group consisting of benzotrichloride, o, m, or p-chlorobenzotrichloride, o, m, or p-fluorobenzotrichloride, o, m, or p-bromobenzotrichloride, o, m, or p-iodobenzotrichloride, 2,4; 2,5; 3,4 or 3,5 dichloro, dibromo, or difluorobenzotrichloride, 2,3,4; 2,3,5 or 3,4,5 trichloro, tribromo or trifluorobenzotrichloride, 2-chloro-4-fluorobenzotrichloride, 2-chloro 4-bromobenzotrichloride; 4-chloro 2-bromobenzotrichloride, 4-chloro-2-fluorobenzotrichloride, 2-chloro-3-bromobenzotrichloride, and 1,3-bis(trichloromethyl)benzene, and 1,4-bis(trichloromethyl)benzene.

11. The process defined in claim 10, wherein the benzene compound having one or more trichloromethyl groups bonded to non-adjacent carbon atoms comprises one selected from the group consisting of benzotrichloride, o, m, or p-chlorobenzotrichloride, o, m, or p-fluorobenzotrichloride, m, or p-bromobenzotrichloride, 3,4 dichlorobenzotrichloride, 1,3-bis(trichloromethyl)benzene, and 1,4-bis(trichloromethyl)benzene.

12. The process defined in claim 1, wherein the aliphatic carboxylic acid anhydride comprises one selected from the group consisting of acetic anhydride, propionic anhydride, butyric anhydride, isobutyric anhydride, valeric anhydride, isovaleric anhydride, pivalic anhydride.

13. The process defined in claim 1, wherein the aliphatic carboxylic acid anhydride comprises one selected from the group consisting of acetic anhydride and propionic anhydride.

14. The process defined in claim 1, wherein the catalyst comprises a concentration between about 0.01 to 10 percent by weight of the aromatic compound having one or more trichloromethyl groups bonded to non-adjacent aromatic carbon atoms.

15. The process defined in claim 1, wherein the concentration of the catalyst comprises between about 0.2 to 1 percent by weight of the aromatic compound charge.

16. A process for preparing benzoyl acid chloride and acetyl chloride comprising the following steps:
   A. mixing an acetic anhydride with trichloromethylbenzene;
   B. heating the mixture in the presence of concentrated sulfuric acid until the acetyl chloride begins to distill;
   C. distilling the acetyl chloride;
   D. heating the reaction mixture further; and
   E. distilling the benzoyl acid chloride.

17. A process for preparing an aromatic acid chloride and an aliphatic carboxylic acid chloride by performing the following chemical reaction:

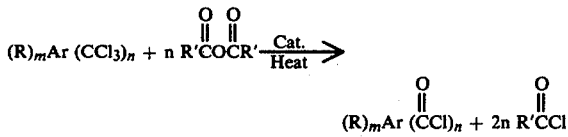

where "R" is selected from the group consisting of hydrogen, chlorine, bromine, fluorine, iodine, alkyl, chloroalkyl, fluoroalkyl, alkoxyl, and carbonyl chloride, "R'" is an aliphatic carbon chain having between one and six carbon atoms, "Ar" is a benzene ring, "m" is equal to 6-n, n is an integer and the catalyst is sulfuric acid.

18. A process for preparing an aromatic acid chloride and an aliphatic acid chloride comprising the following steps:
   A. mixing an aliphatic carboxylic acid anhydride with an aromatic compound having
      (a) between one and three trichloromethyl groups bonded to non-adjacent carbon atoms of the aromatic ring, and
      (b) between 3 and 5 other substituents selected from the group consisting of hydrogen, chlorine, bromine, fluorine, iodine, and carbonyl chloride;
   B. heating the mixture in the presence of a sulfuric acid catalyst until the aliphatic carboxylic acid chloride begins to distill;
   C. distilling the aliphatic carboxylic acid chloride; and
   D. recovering the aromatic acid chloride from the reaction mixture.

19. The process defined in claim 1, wherein the catalyst is sulfuric acid.

* * * * *

UNITED STATES PATENT AND TRADEMARK OFFICE
CERTIFICATE OF CORRECTION

PATENT NO. : 4,163,753

DATED : August 7, 1979

INVENTOR(S) : Philip M. Pivawer

It is certified that error appears in the above-identified patent and that said Letters Patent are hereby corrected as shown below:

Column 2, Line 33, delete "sytem" and substitute therefor --system--.

Column 4, Line 27, delete "expecially" and substitute therefor --especially--.

Column 4, Line 40, delete "R-C=O-O-C=O-R" and substitute therefor $--R-\overset{O}{\overset{\|}{C}}-O-\overset{O}{\overset{\|}{C}}-R--$.

Column 4, Line 43, delete "$(CH_3C=O-O-CH_3)$" and substitute therefor $--(CH_3-\overset{O}{\overset{\|}{C}}-O-\overset{O}{\overset{\|}{C}}-CH_3)--$.

Column 5, Line 55, delete "$(R)_m Ar(CCl_3)_n + nR'-C^{=O}-R'$" and substitute therefor $--(R)_m Ar(CCl_3)_n + nR'-\overset{O}{\overset{\|}{C}}-O-\overset{O}{\overset{\|}{C}}-R'--$.

Column 5, Line 57, delete "$\underset{Heat}{\overset{Cat}{\longrightarrow}} (R)_m Ar(CCl)_n^{=O} +2_n R'-C^{=O}-Cl$" and substitute therefor $--\underset{Heat}{\overset{Cat}{\longrightarrow}} (R)_m Ar(\overset{O}{\overset{\|}{C}}Cl)_n +2_n R'-\overset{O}{\overset{\|}{C}}-Cl--$.

Column 6, Line 64, delete "mixtue" and substitute therefor --mixture--.

UNITED STATES PATENT AND TRADEMARK OFFICE
CERTIFICATE OF CORRECTION

PATENT NO. : 4,163,753
DATED : August 7, 1979
INVENTOR(S) : Philip M. Pivawer

It is certified that error appears in the above-identified patent and that said Letters Patent are hereby corrected as shown below:

Column 8, Line 23, after "88" delete "L".

Column 9, Line 20, delete "aroatic" and substitute therefor --aromatic--.

Signed and Sealed this

*Twenty-fifth* Day of *March 1980*

[SEAL]

*Attest:*

SIDNEY A. DIAMOND

*Attesting Officer*  *Commissioner of Patents and Trademarks*